United States Patent [19]
Gerdes et al.

[11] Patent Number: 5,852,013
[45] Date of Patent: Dec. 22, 1998

[54] SUBSTITUTED ARYLAZADIOXACYCLO ALKENE FUNGICIDES

[75] Inventors: Peter Gerdes, Aachen; Herbert Gayer, Monheim; Dietmar Kuhnt, Burscheid; Ralf Tiemann, Leverkusen; Klaus Stenzel, Düsseldorf, all of Germany

[73] Assignee: Bayer Aktiengesellschaft, Leverkusen, Germany

[21] Appl. No.: 875,032

[22] PCT Filed: Jan. 10, 1996

[86] PCT No.: PCT/EP96/00069

§ 371 Date: Jul. 16, 1997

§ 102(e) Date: Jul. 16, 1997

[87] PCT Pub. No.: WO96/22983

PCT Pub. Date: Aug. 1, 1996

[30] Foreign Application Priority Data

Jan. 23, 1995 [DE] Germany .......................... 19501842.7

[51] Int. Cl.$^6$ .......................... A01N 43/88; C07D 273/02
[52] U.S. Cl. .......................... 514/224.2; 544/65; 548/124
[58] Field of Search .............................. 544/65; 548/124; 514/229.2

[56] References Cited

U.S. PATENT DOCUMENTS 5,679,676 10/1997 Kruger ................................. 514/229.2

OTHER PUBLICATIONS

Patent Abstracts of Japan, vol. 14, No. 544 (C–0784), 4 Dec. 1990 & JP,A,02 233602 (Hokko Chem Ind Co Ltd) 19 Sep. 1990.

Patent Abstracts of Japan, vol.14, No. 126 (C–0699), 9 Mar. 1990 & JP,A,02 001484 (Hokko Chem Ind Co Ltd) 5 Jan. 1990.

Patent Abstracts of Japan, vol. 13, No. 536 (C–660) 29 Nov. 1989 & JP,A,01 221371 (Hokko Chem Ind Co Ltd) 4 Sep. 1989.

*Primary Examiner*—Robert Gerstl
*Attorney, Agent, or Firm*—Sprung Kramer Schaefer & Briscoe

[57] ABSTRACT

The invention relates to novel substituted arylazadioxacycloalkenes, a plurality of processes for their preparation and to their use as fungicides.

10 Claims, No Drawings

SUBSTITUTED ARYLAZADIOXACYCLO ALKENE FUNGICIDES

The invention relates to novel substituted arylazadioxacycloalkenes, a plurality of processes for their preparation and to their use as fungicides.

Certain substituted arylazadioxacycloalkenes are known to have fungicidal properties [cf. Hokko Chemical Industry, JP-A 02001484; cited in Chem. Abstr. 113:6381 (1990)].

However, in many instances the activity of these compounds is unsatisfactory.

This invention, accordingly, provides the novel substituted arylazadioxacycloalkenes of

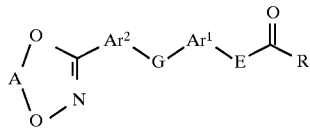

in which

A represents optionally substituted alkylene.

$Ar^1$, $Ar^2$ independently of one another each represent optionally substituted arylene or heteroarylene.

E represents a 1-alkene-1,1-diyl grouping which contains a radical $R^1$ in position 2, or represents a 2-aza-1-alkene-1,1-diyl grouping which contains a radical $R^2$ in position 2, or represents an optionally substituted imino grouping ("azamethylene", N—$R^3$), or represents a 3-aza-1-propene-2,3-diyl grouping which contains a radical $R^4$ in position 1 and a radical $R^5$ in position 3, or represents a 3-aza-1-propene-2,3-diyl grouping which contains a radical $R^4$ in position 1, or represents a 3-thia-1-propene-2,3-diyl grouping which contains a radical $R^4$ in position 1, or represents a 1-aza-1-propene-2,3-diyl grouping which contains a radical $R^6$ in position 1 and a radical $R^5$ in position 3, or represents a 1-aza-1-propene-2,3-diyl grouping which contains a radical $R^4$ in position 1 and a radical $R^5$ in position 3, or represents a 1,3-diaza-1-propene-2,3-diyl grouping which contains a radical $R^6$ in position 1 and a radical $R^5$ in position 3, or represents a 1-aza-3-oxa-1-propene-2,3-diyl grouping which contains a radical $R^6$ in position 1, or represents a 1-aza-3-thia-1-propene-2,3-diyl grouping which contains a radical $R^6$ in position 1, where $R^1$, $R^4$ each represent hydrogen, halogen, cyano or respectively optionally substituted alkyl, alkoxy, alkylthio, alkylamino or dialkylamino, $R^2$, $R^6$ each represent hydrogen, amino, cyano or respectively optionally substituted alkyl, alkoxy, alkylamino or dialkylamino, and $R^3$ represents hydrogen, cyano or respectively optionally substituted alkyl, alkenyl, alkinyl, cycloalkyl or cycloalkylalkyl, $R^5$ represents alkyl, G represents a single bond, represents oxygen, sulphur, or represents respectively optionally halogen-, hydroxyl-, alkyl-, halogenoalkyl- or cycloalkyl-substituted alkanediyl, alkenediyl, alkinediyl or one of the groupings below —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C($R^7$)=N—O—, —C($R^7$)—N—O—CH$_2$—, —N($R^8$)—, —CQ—N($R^8$)—, —N($R^8$)—CQ—, —Q—CQ—N($R^8$)—, —N=C($R^7$)—Q—CH$_2$—, —CH$_2$—O—N=C($R^7$)—, —N($R^8$)—CQ—Q—, —CQ—N($R^8$)—CQ—Q—, —N($R^8$)—CQ—Q—CH$_2$—, —Q—C($R^7$)=N—O—CH$_2$—, —N($R^8$)—C($R^7$)=N—O—CH$_2$—, O—CH$_2$—C($R^7$)=N—O—, —N=N—C($R^7$)—N—O—, —T—Ar$^3$—or —T—Ar$^3$—Q—, where $Ar^3$ represents optionally substituted arylene, heteroarylene, cycloalkylene or heterocycloalkylene (i.e. an aliphatic ring which is attached twice and in which one or more carbon atoms are replaced by hetero atoms, i.e. by atoms different from carbon), n represents the numbers 0, 1 or 2, Q represents oxygen or sulphur, $R^7$ represents hydrogen, cyano or respectively optionally substituted alkyl, alkoxy, alkylthio, alkylamino, dialkylamino or cycloalkyl, and $R^8$ represents hydrogen, hydroxyl, cyano or respectively optionally substituted alkyl, alkoxy or cycloalkyl and T represents a single bond, represents oxygen, sulphur, —CH$_2$—O—, CH$_2$—S— or represents optionally substituted alkanediyl and R represents alkyl, alkoxy, hydroxylamino, alkoxamino, alkylamino or dialkylamino.

Furthermore, it has been found that the novel substituted arylazadioxacycloalkenes of the general formula (I) are obtained when a) hydroxyl compounds of the general formula (II)

in which

A and $Ar^2$ are each as defined above, are reacted with halogen compounds of the general formula (III)

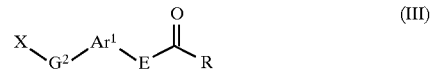

in which $G^2$ represents —Ar$^3$—Q— or represents —Ar—, $Ar^1$, $Ar^3$, E, Q and R are each as defined above and X represents halogen, if appropriate in the presence of an acid acceptor and if appropriate in the presence of a diluent;

b) hydroxyl compounds of the general formula (II)

in which

A and $Ar^2$ are each as defined above, are reacted with halogen compounds of the general formula (IV)

in which $Ar^1$, E and R are each as defined above and

X represents halogen, if appropriate in the presence of an acid acceptor and if appropriate in the presence of a diluent;

c) esters of the general formula (I-1)

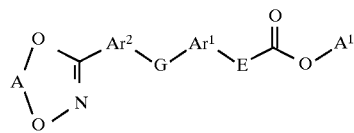

in which
A, Ar¹, Ar², E and G are each as defined above and
A¹ represents alkyl, are reacted with amines of the general formula (V),

in which
A² and A³ independently of one another are each hydrogen, respectively optionally substituted alkyl, alkoxy or hydroxyl,
or an acid addition complex thereof
if appropriate in the presence of an acid acceptor and if appropriate in the presence of a diluent.

Finally, it has been found that the novel substituted carboxamides of the general formula (I) have a very strong fungicidal activity. The compounds according to the invention may optionally be present as mixtures of various possible isomeric forms, in particular of stereoisomers, such as, for example,
E- and Z-isomers. Both the E- and the Z-isomers, and any mixtures of these isomers, are claimed.

The invention preferably relates to compounds of the formula (I) in which
A represents alkylene having 1 to 4 carbon atoms,
Ar¹ represents respectively optionally substituted phenylene or naphthylene, represents mono- or dicyclic heteroarylene having in each case 5 or 6 ring members or represents benzo-fused heteroarylene having 5 or 6 ring members, at least one of which in each case is oxygen, sulphur or nitrogen and one or two more of which optionally are nitrogen, the possible substituents preferably being selected from the list below: halogen, cyano, nitro, amino, hydroxyl, formyl, carboxyl, carbamoyl, thiocarbamoyl, respectively straight-chain or branched alkyl, alkoxy, alkylthio, alkylsulphinyl or alkylsulphonyl having in each case 1 to 6 carbon atoms, respectively straight-chain or branched alkenyl, alkenyloxy or alkinyloxy having in each case 2 to 6 carbon atoms, respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, respectively straight-chain or branched halogenoalkenyl or halogenoalkenyloxy having in each case 2 to 6 carbon atoms and 1 to 13 identical or different halogen atoms, respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, alkylene or dioxyalkylene, each of which has 1 to 6 carbon atoms, is attached twice and is optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms, Ar² represents phenylene or naphthylene or represents heteroarylene having 3 to 7 ring members, each of the radicals being optionally mono- or polysubstituted by identical or different substituents and at least one of the 3 to 7 ring members being oxygen, sulphur or nitrogen and one or two more optionally being nitrogen, the possible substituents preferably being selected from the list below:
halogen, cyano, nitro, amino, hydroxyl, formyl, carboxyl, carbamoyl, thiocarbamoyl;
respectively straight-chain or branched alkyl, alkoxy, alkylthio, alkylsulphinyl or alkylsulphonyl having in each case 1 to 6 carbon atoms;
respectively straight-chain or branched alkenyl or alkenyloxy having in each case 2 to 6 carbon atoms;
respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
respectively straight-chain or branched halogenoalkenyl or halogenoalkenyloxy having in each case 2 to 6 carbon atoms and 1 to 13 identical or different halogen atoms;
respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;
alkylene or dioxyalkylene, each of which has 1 to 6 carbon atoms, is attached twice and is optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms;
cycloalkyl having 3 to 6 carbon atoms;
E represents one of the groupings below:

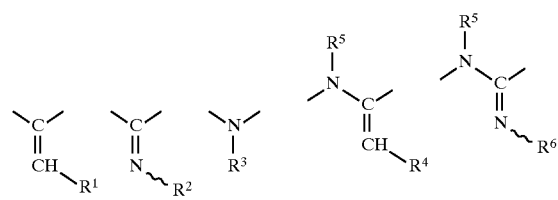

in which
R¹ represents hydrogen, halogen, cyano or represents respectively optionally halogen-, cyano- or $C_1$–$C_4$-alkoxy-substituted alkyl, alkoxy, alkylthio, alkylamino or dialkylamino having in each case 1 to 6 carbon atoms in the alkyl radicals,
R² represents hydrogen, amino, cyano or represents respectively optionally halogen-, cyano- or $C_1$–$C_4$-alkoxy-substituted alkyl, alkoxy, alkylamino or dialkylamino having in each case 1 to 6 carbon atoms in the alkyl radicals,
R³ represents hydrogen, cyano or represents respectively optionally halogen-, cyano- or $C_1$–$C_4$-alkoxy-substituted alkyl, alkenyl or alkinyl having in each case up to 6 carbon atoms or represents respectively optionally halogen-, cyano-, carboxyl-, $C_1$–$C_4$-alkyl- or $C_1$–$C_4$-alkoxy-carbonyl-substituted cycloalkyl or cycloalkylalkyl having 3 to 6 carbon atoms in the cycloalkyl moieties and optionally 1 to 4 carbon atoms in the alkyl moiety, $R^4$ represents hydrogen, halogen, cyano or represents respectively optionally halogen-, cyano- or $C_1$–$C_4$-alkoxy-substituted alkyl, alkoxy, alkylthio, alkylamino or dialkylamino having in each case 1 to 6 carbon atoms in the alkyl radicals, $R^5$ represents alkyl having 1 to 6 carbon atoms and $R^6$ represents hydrogen, amino, cyano or represents respectively optionally halogen-, cyano- or $C_1$–$C_4$-alkoxy-substituted alkyl, alkoxy, alkylamino or dialkylamino having in each case 1 to 6 carbon atoms in the alkyl radicals;

G represents a single bond, represents oxygen, sulphur or represents respectively optionally halogen-, hydroxyl-, $C_1$–$C_4$-alkyl-, $C_1$–$C_4$-halogenoalkyl- or $C_3$–$C_6$-cycloalkyl-substituted alkanediyl, alkenediyl, alkinediyl having in each case up to 4 carbon atoms or one of the groupings below —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)n—CH$_2$—, —C(R$^7$)=N—O—, —C(R7)=N—O—CH$_2$—, —N(R$^8$)—, —CQ—N(R$^8$)—, —N(R$^8$)—CQ—, —Q—CQ—N(R$^8$)—, —N=C(R$^7$)—Q—CH$_2$—, —CH$_2$—O—N=C(R$^7$)—, —N(R$^8$)—CQ—Q—, —CQ—N(R$^8$)—CQ—Q—, —N(R$^8$)—CQ—Q—CH$_2$—, —Q—C(R$^7$)=N—O—CH$_2$—, —N(R$^8$)—C(R$^7$)=N—O—CH$_2$—, —O—CH$_2$—C(R$^7$)=N—O—, —N=N—C(R$^7$)=N—O—, —T—Ar$^3$ or —T—A$^3$—Q—, where n represents the numbers 0, 1 or 2, Q represents oxygen or sulphur, $R^7$ represents hydrogen, cyano, represents respectively optionally halogen-, cyano- or $C_1$–$C_4$-alkoxy-substituted alkyl, alkoxy, alkylthio, alkylamino or dialkylamino having in each case 1 to 6 carbon atoms in the alkyl groups, or represents respectively optionally halogen-, cyano-, carboxyl-, $C_1$–$C_4$-alkyl or $C_1$–$C_4$-alkoxy-carbonyl-substituted cycloalkyl having 3 to 6 carbon atoms, and $R^8$ represents hydrogen, hydroxyl, cyano or represents optionally halogen-, cyano- or $C_1$–$C_4$-alkoxy-substituted alkyl having 1 to 6 carbon atoms, or represents optionally halogen-, cyano-, carboxyl-, $C_1$–$C_4$-alkyl- or $C_1$–$C_4$-alkoxy-carbonyl-substituted cycloalkyl having 3 to 6 carbon atoms and $Ar^3$ represents phenylene, naphthylene, cycloalkylene or represents heteroarylene or heterocycloalkylene having 3 to 7 ring members, each of the radicals being optionally mono- or polysubstituted by identical or different substituents and at least one of the 3 to 7 ring members being oxygen, sulphur or nitrogen and one or two more optionally being nitrogen, the possible substituents preferably being selected from the list below:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, and;

cycloalkyl having 3 to 6 carbon atoms and

T represents a single bond, represents oxygen, sulphur —CH$_2$—O—, CH$_2$—S— or represents alkanediyl having 1 to 3 carbon atoms, R represents alkyl, alkoxy, alkylamino, hydroxylamino, alkoxyamino or dialkylamino having in each case 1 to 4 carbon atoms.

In the definitions, the saturated or unsaturated hydrocarbon chains, such as alkyl, alkanediyl, alkenyl, or alkinyl are in each case, even in combination with hetero atoms, such as in alkoxy, alkylthio or alkylamino, straight-chain or branched.

Halogen generally represents fluorine, chlorine, bromine or iodine, preferably fluorine, chlorine or bromine, in particular fluorine or chlorine.

The invention relates in particular to compounds of the formula (I) in which

A represents methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-i-butylene, $Ar^1$ represents respectively optionally substituted ortho-, meta- or para-phenylene, represents furanediyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl (in particular pyridine-2,3-diyl), pyrimidinediyl, pyridazinediyl, pyrazinediyl, 1,3,4-triazinediyl or 1,2,3-triazinediyl, the possible substituents in particular being selected from the list below:

fluorine, chlorine, cyano, methyl, ethyl, cyclopropyl, trifluoromethyl, methoxy, ethoxy, methylthio, methylsulphinyl or methylsulphonyl, $Ar^2$ represents phenylene, naphthylene, furanediyl, thiophenediyl, oxazolediyl, isoxazolediyl, thiazolediyl, isothiazolediyl, 1,2,4-oxadiazolediyl, 1,3,4-oxadiazolediyl, 1,2,4-thiadiazolediyl, 1,3,4-thiadiazolediyl, pyridinediyl, pyrimidinediyl, pyridazinediyl, pyrazinediyl, 1,2,3-triazinediyl, 1,2,4-triazinediyl, 1,3,5-triazinediyl, each of which is optionally mono- to trisubstituted by identical or different substituents, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

E represents one of the groupings below:

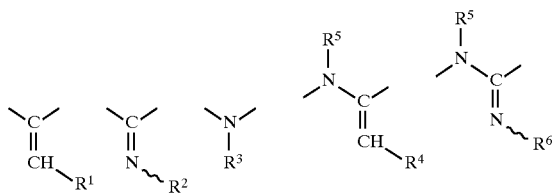

in which
R¹ represents hydrogen, fluorine, chlorine, bromine, cyano or represents respectively optionally fluorine-, chlorine-, cyano-, methoxy- or ethoxy- substituted methyl, ethyl, propyl, methoxy, ethoxy, methylthio, ethylthio, methylamino, ethylamino or dimethylamino, R² represents hydrogen, amino, cyano or represents respectively optionally fluorine-, chlorine-, cyano-, methoxy- or ethoxy-substituted methyl, ethyl, methoxy, ethoxy, methylamino, ethylamino or dimethylamino, R³ represents hydrogen, cyano or represents respectively optionally fluorine-, cyano-, methoxy- or ethoxy-substituted methyl, ethyl, n- or i-propyl, n-, i- or s-butyl, represents allyl or propargyl or represents respectively optionally fluorine-, chlorine-, cyano-, carboxyl-, methyl-, ethyl-, n- or i-propyl-, methoxy-carbonyl- or ethoxy-carbonyl-substituted cyclopropyl, cyclobutyl, cyclopentyl, cyclohexyl, cyclopropylmethyl, cyclobutylmethyl, cyclopentylmethyl or cyclohexylmethyl, R⁴ represents hydrogen, fluorine, chlorine, bromine, cyano or represents respectively optionally fluorine-, chlorine-, cyano-, methoxy- or ethoxy- substituted methyl, ethyl, propyl, methoxy, ethoxy, methylthio, ethylthio, methylamino, ethylamino or dimethylamino, R⁵ represents methyl, ethyl, n- or i-propyl, n-, i- or s-butyl, R⁶ represents hydrogen, amino, cyano or represents respectively optionally fluorine-, chlorine-, cyano-, methoxy- or ethoxy-substituted methyl, ethyl, methoxy, ethoxy, methylamino, ethylamino or dimethylamino, and G represents a single bond, represents oxygen, sulphur, or represents respectively optionally fluorine-, chlorine-, bromine-, hydroxyl-, methyl-, ethyl-, n- or i-propyl-, trifluoromethyl-, cyclopropyl-, cyclobutyl-, cyclopentyl- or cyclohexyl-substituted methylene, dimethylene (ethane-1,2-diyl), ethene-1,2-diyl, ethine-1,2-diyl or one of the groupings below —Q—CQ—, —CQ—Q—, —CH₂—Q—; —Q—CH₂—, —CQ—Q—CH₂—, —CH₂—Q—CQ—, —Q—CQ—CH₂—, —Q—CQ—Q—CH₂—, —N═N—, —S(O)ₙ—, —CH₂—S(O)ₙ—, —CQ—, —S(O)ₙ—CH₂—, —C(R⁷)═N—O—, —C(R7)═N—O—CH₂—, —N(R⁸)—, —CQ—N(R⁸)—, —N(R⁸)—CQ—, —Q—CQ—N(R⁸)—, —N═C(R⁷)—Q—CH₂—, —CH₂—O—N═C(R⁷)—, —N(R⁸)—CQ—Q—, —CQ—N(R⁸)—CQ—Q—, —N(R⁸)—CQ—Q—CH₂—, —Q—C(R⁷)═N—O—CH₂—, —N(R⁸)—C(R⁷)═N—O—CH₂—, —O—CH₂—C(R⁷)═N—O—, —N═N—C(R⁷)═N—O—, —T—Ar³— or —T—Ar³—Q—, where n represents the numbers 0, 1 or 2,
Q represents oxygen or sulphur,
R⁷ represents hydrogen, cyano, represents respectively optionally fluorine-, chlorine-, cyano-, methoxy- or ethoxy-substituted methyl, ethyl, n- or i-propyl, n-, i- or s-butyl, methoxy, ethoxy, propoxy, butoxy, methylthio, ethylthio, propylthio, butylthio, methylamino, ethylamino, propylamino, dimethylamino or diethylamino or represents respectively optionally fluorine-, chlorine-, cyano-, carboxyl-, methyl-, ethyl-, n- or i-propyl-, methoxycarbonyl- or ethoxy-carbonyl-substituted cyclopropyl, cyclobutyl, cyclopentyl or cyclohexyl, and R⁸ represents hydrogen, hydroxyl, cyano or represents respectively optionally fluorine-, chlorine-, cyano-, methoxy- or ethoxy-substituted methyl, ethyl, n- or i-propyl, n-, i-, s- or t-butyl or represents respectively optionally fluorine-, chlorine-, cyano-, carboxyl-, methyl-, ethyl-, n- or i-propyl-, methoxy-carbonyl- or ethoxy-carbonyl-substituted cyclopropyl, cyclobutyl, cyclopentyl or cyclohexyl, Ar³ represents phenylene, naphthylene, furanediyl, thiophenediyl, oxazolediyl, isoxazolediyl, thiazolediyl, isothiazolediyl, 1,2,4-oxadia-zolediyl, 1,3,4-oxadiazolediyl, 1,2,4-thiadiazolediyl, 1,3,4-thiadiazolediyl, pyridinediyl, pyrimidinediyl, pyridazinediyl, pyrazinediyl, 1,2,3-triazinediyl, 1,2,4-triazinediyl, 1,3,5-triazinediyl, oxiranediyl, oxetanediyl, tetrahydrofuranediyl, perhydropyranediyl or pyrrolidinediyl, each of which is optionally mono- to trisubstituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, , acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl, ethoximinoethyl or cyclopropyl and T represents a single bond, represents oxygen, sulphur, —CH₂—O—, CH₂—S—, methylene, ethylene or propylene and R represents methyl, ethyl, n- or i-propyl, methoxy, ethoxy, n- or i-propoxy, methylamino, ethylamino, n- or i-propylamino, hydroxylamino, methoxyamino, dimethylamino, diethylamino.

Very particular preference is given to compounds of the general formula (I) in which A represents methylene, 1,1-ethylene, 1,2-ethylene, 1,2- or 1,3-propylene, Ar¹ represents ortho-phenylene, pyridine-2,3-diyl or thiophene-2,3-diyl, Ar² represents phenylene which is in each case optionally mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluomethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, methylenedioxy or ethylenedioxy, each of which is attached twice and each of which is optionally mono- to tetrasubstituted by identical or different substituents from the group consisting of fluorine, chlorine, methyl, trifluoromethyl or ethyl, E represents one of the groupings below

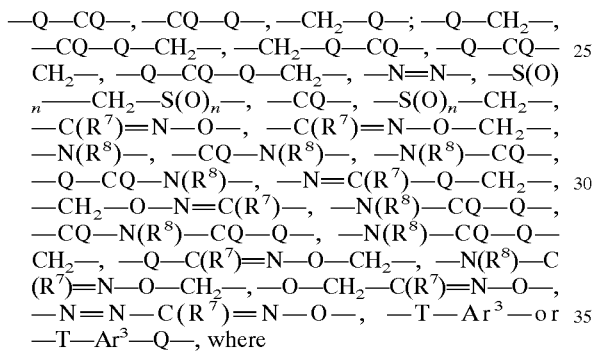

in which $R^1$ and $R^2$ each represent methoxy and $R^3$ represents hydrogen, cyano, methyl, ethyl, n- or i-propyl, methoxy or ethoxy, G represents oxygen or represents respectively optionally fluorine-, chlorine- or bromine-substituted dimethylene (ethane-1,2-diyl), ethene-1,2-diyl or one of the groupings below —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N═N—, —S(O)$_n$——CH$_2$—S(O)$_n$—, —CQ—, —S(O)$_n$—CH$_2$—, —C(R$^7$)═N—O—, —C(R$^7$)═N—O—CH$_2$—, —N(R$^8$)—, —CQ—N(R$^8$)—, —N(R$^8$)—CQ—, —Q—CQ—N(R$^8$)—, —N═C(R$^7$)—Q—CH$_2$—, —CH$_2$—O—N═C(R$^7$)—, —N(R$^8$)—CQ—Q—, —CQ—N(R$^8$)—CQ—Q—, —N(R$^8$)—CQ—Q—CH$_2$—, —Q—C(R$^7$)═N—O—CH$_2$—, —N(R$^8$)—C(R$^7$)═N—O—CH$_2$—, —O—CH$_2$—C(R$^7$)═N—O—, —N═N—C(R$^7$)═N—O—, —T—Ar$^3$—or —T—Ar$^3$—Q—, where n represents the numbers 0, 1 or 2, Q represents oxygen or sulphur, $R^7$ represents hydrogen, cyano, methyl, ethyl or cyclopropyl, and $R^8$ represents hydrogen, methyl, ethyl or cyclopropyl, Ar$^3$ represents phenylene, 1,2,4-thiadiazolediyl, 1,3,4-thiadiazolediyl, 1,2,4-oxadiazolediyl, 1,3,4-oxadiazolediyl, pyridinediyl, pyrimidinediyl, pyridazinediyl, pyrazinediyl, 1,2,3-triazinediyl, 1,2,4-triazinediyl- or 1,3,5-triazinediyl, each of which is optionally mono- to trisubstituted by identical or different substituents, the possible substituents preferably being selected from the list below:

fluorine, chlorine, bromine, cyano, methyl, ethyl, n- or i-propyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, and T represents a single bond, represents oxygen, sulphur, —CH$_2$—O—, CH$_2$—S—, methylene, ethylene or propylene and R represents methyl, ethyl, methoxy, methylamino or hydroxylamino.

A particularly preferred group of compounds according to the invention are those compounds of the formula (I) in which A represents methylene, 1,1-ethylene, 1,2-ethylene, 1,2- or 1,3-propylene, Ar$^1$ represents ortho-phenylene, pyridine-2,3-diyl or thiophene-2,3-diyl, Ar$^2$ represents phenylene which is in each case optionally mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluomethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, methylenedioxy or ethylenedioxy, each of which is attached twice and each of which is optionally mono- to tetrasubstituted by identical or different substituents from the group consisting of fluorine, chlorine, methyl, trifluoromethyl or ethyl, E represents one of the groupings below

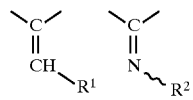

in which $R^1$ and $R^2$ each represent methoxy and

G represents —O—CH$_2$ and

R represents methyl, ethyl, methoxy, methylamino or hydroxylamino.

Also very particularly preferred are compounds of the general formula (I)

in which

A represents methylene, 1,1-ethylene, 1,2-ethylene, 1,2- or 1,3-propylene,

Ar$^1$ represents ortho-phenylene, pyridine-2,3-diyl or thiophene-2,3-diyl,

Ar$^2$ represents phenylene which is in each case optionally mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluomethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, methylenedioxy or ethylenedioxy, each of which is attached twice and each of which is optionally mono- to tetrasubstituted by identical or different substituents from the group consisting of fluorine, chlorine, methyl, trifluoromethyl or ethyl, E represents one of the groupings below

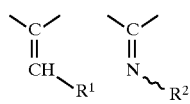

in which
R¹ and R² each represent methoxy and
G represents —C(R7)=N—O—CH₂—where
R⁷ represents hydrogen, cyano, methyl, ethyl or cyclopropyl and
R represents methyl, ethyl, methoxy, methylamino or hydroxylamino.

Furthermore, very particular preference is given to compounds of the general formula
in which
A represents methylene, 1,1-ethylene, 1,2-ethylene, 1,2- or 1,3-propylene,
Ar¹ represents ortho-phenylene,
Ar² represents phenylene which is in each case optionally mono- to trisubstituted by identical or different substituents, the possible substituents preferably being selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluomethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl,
methylenedioxy or ethylenedioxy, each of which is attached twice and each of which is optionally mono- to tetrasubstituted by identical or different substituents from the group consisting of fluorine, chlorine, methyl, trifluoromethyl or ethyl, E represents one of the groupings below:

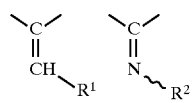

in which
R¹ and R² each represent methoxy,
G represents —T—Ar—Q—where
Q represents oxygen or sulphur,
Ar³ represents 1,2,4-thiadiazolediyl, 1,3,4-thiadiazolediyl, 1,2,4-oxadiazolediyl, 1,3,4-oxadiazolediyl or represents pyridinediyl, pyrimidinediyl or 1,3,5-triazinediyl, each of which is optionally mono- or disubstituted by identical or different substituents from the group consisting of fluorine, chlorine, cyano, methyl, cyclopropyl, methoxy, methylthio, trifluoromethyl, difluoromethoxy, trifluoromethoxy, difluorochloromethoxy,
T represents a single bond, represents oxygen, sulphur, —CH₂—O—, CH₂—S—, methylene, ethylene or propylene and
R represents methyl, ethyl, methoxy, methylamino or hydroxylamino.

The abovementioned general or preferred radical definitions apply both to the end products of the formula (I) and, correspondingly, to the starting materials or intermediates required in each case for preparation.

These radical definitions can be combined with each other as desired, that is to say combinations between the ranges stated for preferred compounds are also possible.

Examples of the compounds according to the invention are listed in Table 1 with reference to the general formula Ia:

TABLE 1

| Z | G | Ar¹ | E | R |
|---|---|-----|---|---|
| ![structure] | —O—CH₂— | ![phenyl] | ![vinyl] | OCH₃ |
| ![structure] | —O—CH₂— | ![phenyl] | ![imino] | OCH₃ |

TABLE 1-continued (Structural formula: Z—G—Ar¹—E—C(=O)—R, (Ia))

| Z | G | Ar¹ | E | R |
|---|---|---|---|---|
| (4-substituted phenyl with 1,4,2-dioxazine ring, C=N, carbonyl) | —O—CH₂— | (1,2-phenylene) | C(CH₃)=N—OCH₃ | NHCH₃ |
| (3-substituted phenyl with 1,4,2-dioxazine ring) | —O—CH₂— | (1,2-phenylene) | C(CH₃)=CH—OCH₃ | OCH₃ |
| (3-substituted phenyl with 1,4,2-dioxazine ring) | —O—CH₂— | (1,2-phenylene) | C(CH₃)=N—OCH₃ | OCH₃ |
| (3-substituted phenyl with 1,4,2-dioxazine ring) | —O—CH₂— | (1,2-phenylene) | C(CH₃)=N—OCH₃ | NHCH₃ |
| (3-substituted phenyl with 1,4,2-dioxazine ring) | C(CH₃)=N—O— | (1,2-phenylene) | C(CH₃)=CH—OCH₃ | OCH₃ |
| (3-substituted phenyl with 1,4,2-dioxazine ring) | C(CH₃)=N—O— | (1,2-phenylene) | C(CH₃)=N—OCH₃ | OCH₃ |
| (3-substituted phenyl with 1,4,2-dioxazine ring) | C(CH₃)=N—O— | (1,2-phenylene) | C(CH₃)=N—OCH₃ | NHCH₃ |
| (3-substituted phenyl with 1,4,2-dioxazine ring) | 4,6-dimethoxypyrimidin-5-yl (via O linkages) | (1,2-phenylene) | C(CH₃)=CH—OCH₃ | OCH₃ |

TABLE 1-continued (structure Ia shown: Z-G-Ar¹-E-C(=O)-R)

| Z | G | Ar¹ | E | R |
|---|---|---|---|---|
| (cyclic O-N-C(=O)-phenyl) | N=CH-N with OCH₃ | phenyl | C=C(OCH₃) | OCH₃ |
| (cyclic O-N-C(=O)-phenyl) | N-S with two OCH₃ | phenyl | C=C(OCH₃) | OCH₃ |
| (cyclic O-N-C(=O)-phenyl) | N-S with OCH₃ | phenyl | C=C(OCH₃) | OCH₃ |
| (cyclic O-N-C(=O)-phenyl) | N-O with OCH₃ | phenyl | C=C(OCH₃) | OCH₃ |

The hydroxyl compounds required as starting materials to carry out the processes a) and b) according to the invention are defined in a general way by the formula (II). In this formula (II), A and Ar² each preferably or in particular have those meanings already given in connection with the description of the compounds of the formula (I) according to the invention as preferred or as particularly preferred for A and Ar².

The hydroxyl compounds of the formula (II) are known and/or can be prepared by known processes (cf. JP-A 02001484).

The halogen compounds further required as starting materials to carry out the process a) according to the invention are defined in a general way by the formula (III). In this formula (III), Ar¹, Ar³, E, Q and R each preferably or in particular have those meanings already given in connection with the description of the compounds of the formula (I) according to the invention as preferred or as particularly preferred for Ar¹, Ar³, E, Q and R. X represents halogen, preferably chlorine or fluorine.

The halogen compounds of the formula (III) are known and/or can be prepared by known processes (cf. EP-A 382375).

The halogen compounds further required as starting materials to carry out the process b) according to the invention are defined in a general way by the formula (IV). In this formula (IV), Ar¹, E and R each preferably or in particular have those meanings already given in connection with the description of the compounds of the formula (I) according to the invention as preferred or as particularly preferred for Ar¹, E and R. X represents halogen, preferably chlorine or bromine.

The halogen compounds of the formula (IV) are known and/or can be prepared by known processes (cf. EP-A 226917 and EP-A 254426).

The esters required as starting materials to carry out the process c) according to the invention are defined in a general way by the formula (I-1). In this formula (I-1), A, Ar¹, Ar², E and G each preferably or in particular have those meanings already given in connection with the description of the compounds of the formula (I) according to the invention as preferred or as particularly preferred for A, Ar¹, Ar², E and G. A¹ represents alkyl, preferably methyl. The compounds of the formula (I-1) are compounds according to the invention and can be obtained by the processes (a) and (b) according to the invention.

The amines further required as starting materials to carry out the process (c) according to the invention are defined in a general way by the formula (V). In the formula (V), A² an A³ independently of one another each represent hydrogen, respectively optionally substituted alkyl, alkoxy or hydroxyl, A² preferably represents hydrogen, A³ preferably represents methyl or hydroxyl. The amines of the formula (V) or their acid addition complexes are known reagents in organic chemistry.

The processes a), b) and c) according to the invention are, if appropriate, carried out in the presence of a diluent. Suitable diluents are all inert organic solvents. These are preferably aliphatic, alicyclic or aromatic hydrocarbons, such as, for example petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxan, tetrahydrofuran, 1,2- dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate, or ethyl acetate; sulphoxides, such as dimethyl sulphoxide or sulphones, such as sulpholane. The process c) according to the invention can, if appropriate, also be carried out in alcohols, such as methanol, ethanol, n- or i-propanol, n-, i-, sec- or t-butanol, ethanediol, propane-1,2-diol, ethoxyethanol, methoxyethanol, diethylene glycol monomethyl ether, diethylene glycol monoethyl ether, their mixtures with water or in pure water.

The processes a), b) and c) according to the invention are, if appropriate, carried out in the presence of a suitable acid acceptor. Suitable acid acceptors are all customary inorganic or organic bases. These are, for example alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazaobicyclononene (DBN) or diazabicycloundecene (DBU).

When carrying out the process according to the invention, the reaction temperatures may be varied over a relatively wide range. In general, temperatures between −20° C. and +200° C. are employed. Processes a) and b) are preferably carried out at temperatures between 20° C. and 150° C., process c) is preferably carried out at temperatures of 0°–80° C.

The processes a) and b) according to the invention for preparing the compounds of the formula (I) according to the invention are carried out by employing generally 0.5 to 5 mol, preferably 0.8 to 1.5 mol, of halogen compound of the formula (III) or (IV) per mole of hydroxyl derivative of the formula (II).

The process c) according to the invention for preparing the compounds of the formula (I) according to the invention is carried out by employing generally 1 to 100 mol, preferably 1 to 20 mol, of amine of formula (V) per mole of ester of the formula (I-1).

The reaction is carried out and the reaction products are worked up and isolated according to known processes (cf. also the Preparation Examples).

The active compounds according to the invention have a potent microbicidal activity and are employed in practice for controlling undesirable microorganisms. The active compounds are suitable for use as crop protection agents, in particular as fungicides.

Fungicides are employed in crop protection for controlling Plasmodiophoromycetes, Oomycetes, Chytridiomycetes, Zygomycetes, Ascomycetes, Basidiomycetes and Deuteromycetes.

Some pathogens causing fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidial form: Drechslera, synonym: Helminthosporium);

Cochliobolus species, such as, for example, *Cochliobolus sativus* (conidiae form: Drechslera, synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in viticulture, fruit-growing and horticulture, such as, for example, against Plasmopara species and Podosphaera species.

The active compounds according to the invention are also employed very successfully for controlling cereal diseases, such as, for example, against Septoria species, Pyricularia species, Pyrenophora species and Cochliobolus species.

Furthermore, the active compounds according to the invention have an excellent in vitro activity. Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cold and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water; liquefied gaseous extenders or carriers are to be understood as meaning liquids which are gaseous at ambient temperature and under atmospheric pressure, for example aerosol propellants such as halogenated hydrocarbons, or else butane, propane, nitrogen and carbon dioxide; suitable solid carriers are: for example, ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example, crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc. The formulations generally comprise between 0.1 and 95 per cent by weight of active compound, preferably between 0.5 and 90%.

The active compounds according to the invention can be used as such or, in their formulations, also as a mixture with known fungicides, bactericides, acaricides, nematicides or insecticides in order thus, for example, to widen the spectrum of action or to prevent development of resistance.

In many cases, synergistic effects are achieved.

Examples of co-components in mixtures are the following compounds:

Fungicides:

2-aminobutane; 2-anilino-4-methyl-6-cyclopropyl-pyrimidine; 2',6'-dibromo-2-methyl-4'-trifluoromethoxy-4'-trifluoro-methyl- 1 ,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cypro-conazole, cyprofuram, dichlorophen, diclobutrazol, diclofluanid, diclomezine, dicloran, diethofencarb,difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin,
zineb, ziram.

Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157419, CGA 184699, chloethocarb, chlorethoxyfos, chloretoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emarnectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenfos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, pernethrin, phenthoate, phorate, phosalone, phosmet, phosphamdon, phoxim, pirimicarb, pirimiphos M, ,primiphos A, profenofos, profenophos, promecarb, propaphos, propoxur, prothiofos, prothiophos, prothoate, pymetrozin, pyrachlophos, pyraclofos, pyraclophos, pyradaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

It is also possible to admix other known active compounds, such as herbicides, or fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by wetting, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

PREPARATION EXAMPLES

Example 1

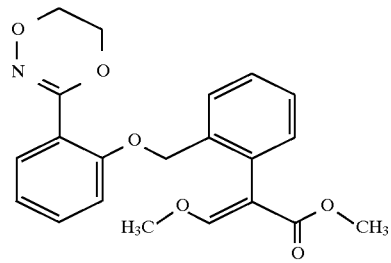

2.85 g (0.01 mol) of methyl 2-(2-bromomethylphenyl)-3-methoxyacrylate, 1.8 g (0.01 mol) of 3-(2-hydroxyphenyl)-5,6-dihydro-1,4,2-dioxazine and 1.3 g of potassium tert-butoxide in 50 ml of tetrahydrofuran are heated under reflux for 4 hours. The solution is then evaporated to dryness, taken up in 50 ml of water and extracted with ethyl acetate. The organic phase is dried and concentrated under reduced pressure. Finally, the residue is purified by column chromatography over silica gel using dichloromethane/ethyl acetate (10:1).

2.9 g (76.3%) of the target compound are obtained as a pale yellow oil.

$^1$H NMR (CDCl$_3$/TMS)δ(ppm): 3.71 (s,3 H), 3.82 (s,3 H), 4.20 (m,2 H), 4.47 (m,2 H), 5.04 (s,2 H), 6.75–7.5 (m,8 H), 7.61 (s,1 H).

Example 2

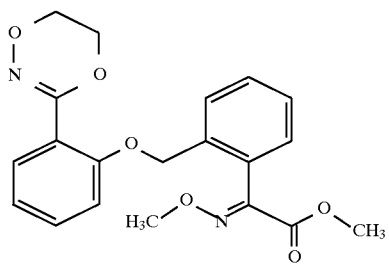

8.6 g (0.03 mol) of methyl 2-(2-bromomethylphenyl)-2-methoximinoacetate, 5.4 g (0.03 mol) of 3-(2-hydroxyphenyl)-5,6-dihydro-1,4,2-dioxazine and 1 g (0.033 mol) of sodium hydride (80%) in 50 ml of tetrahydrofuran are heated under reflux for 4 hours. The solution is then evaporated to dryness, taken up in 50 ml of water and extracted with ethyl acetate. The organic phase is dried and concentrated under reduced pressure. Finally, the residue is purified by column chromatography over silica gel using dichloromethane/ethyl acetate (10:1).

3.5 g (31%) of the target compound are obtained as a white solid.

Melting point: 179° C.

Example 3

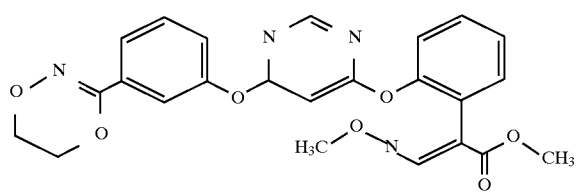

At room temperature, 0.7 g (0.022 mol) of 80% sodium hydride are added with stirring to a mixture of 6.4 g (0.02 mol) of methyl E-3-methoxy-2-[2-(6-chloro-4-pyrimidinyloxy)-phenyl]acrylate (cf. for example EP 382375) and 3.6 g (0.02 mol) of 3-(3-hydroxyphenyl)-5,6-dihydro-1,4,2-dioxazine in 50 ml of absolute N,N-dimethylformamide, and the mixture is stirred for a further 16 hours at room temperature. For work-up, the mixture is poured into a half-concentrated ammonium chloride solution and extracted twice with 100 ml of methyl t-butyl ether each time. The combined organic phases are dried and concentrated under reduced pressure, and the residue is purified by column chromatography over silica gel using (dichloromethane/ethyl acetate 10: 1).

6.9 g (74.5% of theory) of methyl E-3-methoxy-2-{2-[6-(3-<5,6-dihydro-1,4,2-dioxazinyl>-phenoxy)-4-pyrimidinyloxy]-phenyl}-acrylate are obtained as an oil.

$^1$H NMR (CDCl$_3$/TMS)δ(ppm): 3.61 (s,3 H), 3.75 (s,3 H), 4.20 (m,2 H), 4.51 (m,2 H),

Example 4

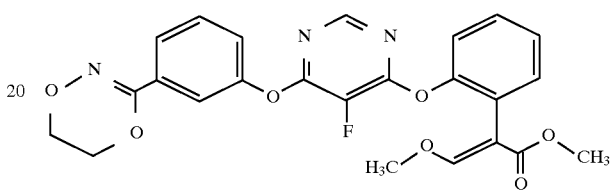

MethylE-3-methoxy-2-[2-(6-chloro-4-pyrimidinyloxy)-phenyl]acrylate 6.4 g (0.02 mol) of methyl E-3-methoxy-2-[2-(5-fluoro-6-chloro-4-pyrimidinyloxy)-phenyl]acrylate, 3.6 g (0.02 mol) of 3-(3-hydroxyphenyl)-5,6-dihydro-1,4,2-dioxazine and 2.7 g (0.024 mol) of potassium t-butoxide in 50 ml of tetrahydrofuran are heated under reflux for 4 hours. The solution is then evaporated to dryness, taken up in 50 ml of water and extracted with ethyl acetate. The organic phase is dried and concentrated under reduced pressure. Finally, the residue is purified by column chromatography over silica gel using dichloromethane/ethyl acetate (10:1). 1.5 g (15.6%) of the target compound are obtained as a pale yellow oil.

$^1$H NMR (CDCl$_3$/TMS)δ(ppm): 3.63 (s,3 H), 3.79 (s,3 H), 4.11 (m,2H), 4.39 (m,2 H), Similarly to Examples 1 to 4, and according to the general description of the preparation processes according to the invention, the compounds listed in Table 2 below, for example, can also be prepared:

TABLE 2

$$Z-G-Ar^1-E-\overset{O}{\underset{}{C}}-R$$
(Ia)

| Ex. No. | Z | G | Ar$^1$ | E | R | physical constants |
|---|---|---|---|---|---|---|
| 5 | ![structure] | —O—CH$_2$— | ![phenyl] | 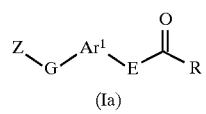 | OCH$_3$ | $^1$H NMR (CDCl$_3$/TMS): 3.69(s, 3H), 3.81(s, 3H), 4.18(m, 2H), 4.49(m, 2H), 4.96(s, 2H), |

TABLE 2-continued

Structure (Ia): Z–G–Ar¹–E–C(=O)–R

| Ex. No. | Z | G | Ar¹ | E | R | physical constants |
|---|---|---|---|---|---|---|
| 6 | (4-substituted phenyl with fused dihydro-oxazine: O–N ring) | –O–CH₂– | 1,2-phenylene | =C(OCH₃)– | OCH₃ | ¹H NMR (CDCl₃/TMS): 3.69(s, 3H), 3.81(s, 3H), 4.16(m, 2H), 4.48(m, 2H), 4.98(s, 2H), |
| 7 | (3-substituted phenyl with dihydro-oxazine: O–N ring, C=O) | –O–C(F)=C(–O–)–N=CH–N= (fluoropyrimidine linker) | 1,2-phenylene | =C(OCH₃)– | OCH₃ | |
| 8 | (3-substituted phenyl with dihydro-oxazine: O–N ring, C=O) | –O–CH₂– | 1,2-phenylene | =N–OCH₃ | OCH₃ | Mp.: 119° C. |
| 9 | (4-substituted phenyl with fused dihydro-oxazine: O–N ring) | –O–C(F)=C(–O–)–N=CH–N= (fluoropyrimidine linker) | 1,2-phenylene | =C(OCH₃)– | OCH₃ | 1H NMR: 3.64(s, 3H), 3.79(s, 3H), 4.21(m, 2H), 4.53(m, 2H), |
| 10 | (4-substituted phenyl with fused dihydro-oxazine: O–N ring) | –O–C(–O–)=C–N=CH–N= (pyrimidine linker) | 1,2-phenylene | =C(OCH₃)– | OCH₃ | 1H NMR: 3.63(s, 3H), 3.79(s, 3H), 4.11(m, 2H), 4.39(m, 2H) |

Example A

Plasmopara test (vines)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and -the concentrate is diluted with water to the desired concentration.

To test for protective activity, young plants are sprayed with the preparation of active compound. After the spray coating has dried on, the plants are inoculated with an aqueous spore suspension of *Plasmopara viticola* and they then remain for 1 day in a humid chamber at 20° to 22° C. and 100% of relative atmospheric humidity. The plants are then kept for 5 days in a greenhouse at 21° C. and about 90% of atmospheric humidity. The plants are then moistened and kept for 1 day in a humid chamber.

Evaluation is carried out 6 days after the inoculation.

In this test, an efficacy of up to 98% is shown, for example, by the following compounds (3), (5) and (8) at an active compound concentration of 100 ppm.

Example B

Podosphaera test (apple)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound to run-off point. After the spray coating has dried on, the plants are inoculated by dusting with conidia of the causative organism of apple mildew (*Podosphaera leucotricha*).

The plants are then placed in a greenhouse at 23° C. and relative atmospheric humidity of about 70%.

Evaluation is carried out 10 days after the inoculation.

In this test, an efficacy of up to 100% is shown, for example, by the following compounds of Preparation Examples (2), (3), (5) and (7) at an active compound concentration of 100 ppm.

We claim:
1. Compounds of the formula (I)

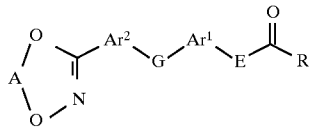

in which

A represents optionally substituted alkylene.

Ar¹, Ar² independently of one another each represent optionally substituted arylene or heteroarylene.

E represents a 1-alkene-1,1-diyl grouping which contains a radical $R^1$ in position 2, or represents a 2-aza-1-alkene-1,1-diyl grouping which contains a radical $R^2$ in position 2, or represents an optionally substituted imino grouping N—$R^3$, or represents a 3-aza-1-propene-2,3-diyl grouping which contains a radical $R^4$ in position 1 and a radical $R^5$ in position 3, or represents a 3-aza-1-propene-2,3-diyl grouping which contains a radical $R^4$ in position 1, or represents a 3-thia-1-propene-2,3-diyl grouping which contains a radical $R^4$ in position 1, or represents a 1-aza-1-propene-2,3-diyl grouping which contains a radical $R^6$ in position 1 and a radical $R^5$ in position 3, or represents a 1-aza-1-propene-2,3-diyl grouping which contains a radical $R^4$ in position 1 and a radical $R^5$ in position 3, or represents a 1,3-diaza-1-propene -2,3-diyl grouping which contains a radical $R^6$ in position 1 and a radical $R^5$ in position 3, or represents a 1-aza-3-oxa-1-propene-2,3-diyl grouping which contains a radical $R^6$ in position 1, or represents a 1-aza-3-thia-1-propene-2,3-diyl grouping which contains a radical $R^6$ in position 1, wherein $R^1$, $R^4$ each represent hydrogen, halogen, cyano or represent optionally substituted alkyl, alkoxy, alkylthio, alkylamino or dialkylamino, $R^2$, $R^6$ each represent hydrogen, amino, cyano or represent optionally substituted alkyl, alkoxy, alkylamino or dialkylamino, and $R^3$ represents hydrogen, cyano or represents optionally substituted alkyl, alkenyl, alkinyl, cycloalkyl or cycloalkylalkyl, $R^5$ represents alkyl, G represents a single bond, represents oxygen, sulphur, or represents optionally halogen-, hydroxyl-, alkyl-, halogenoalkyl- or cycloalkyl-substituted alkanediyl, alkenediyl, alkinediyl or represents a substitustent selected from the group of consisting of
—Q—CQ—, —CQ—Q—, —CH₂—Q—; —Q—CH₂—, —CQ—Q—CH₂—, —CH₂—Q—CQ—, —Q—CQ—CH₂—, —Q—CQ—Q—CH₂—, —N=N—, —S(O)ₙ—, —CH₂—S(O)ₙ—, —CQ—, —S(O)ₙ—CH₂—, —C(R⁷)=N—O—, —C(R⁷)—N—O—CH₂—, —N(R⁸)—, —CQ—N(R⁸)—, —N(R⁸)—CQ—, —Q—CQ—N(R⁸)—, —N=C(R⁷)—Q—CH₂—, —CH₂—O—N=C(R⁷)—, —N(R⁸)—CQ—Q—, —CQ—N(R⁸)—CQ—Q—, —N(R⁸)—CQ—Q—CH₂—,—Q—C(R⁷)=N—O—CH₂—, —N(R⁸)—C(R⁷)=N—O—CH₂—, O—CH₂—C(R⁷)=N—O—,—N=N—C(R⁷)—N—O—, —T—Ar³—and —T—Ar³—Q—, wherein Ar³ represents optionally substituted arylene, heteroarylene, cycloalkylene or heterocycloalkylene, n represents the numbers 0, 1 or 2, Q represents oxygen or sulphur, $R^7$ represents hydrogen, cyano or respectively optionally substituted alkyl, alkoxy, alkylthio, alkylamino, dialkylamino or cycloalkyl, and $R^8$ represents hydrogen, hydroxyl, cyano or respectively optionallysubstituted alkyl, alkoxy or cycloalkyl and T represents a single bond, represents oxygen, sulphur, —CH₂—O—, CH₂—S— or represents optionally substituted alkanediyl and R represents alkyl, alkoxy, hydroxylamino, alkoxamino, alkylamino or dialkylamino.

2. Compounds of the formula (I) according to claim 1 in which

A represents alkylene having 1 to 4 carbon atoms,

Ar¹ represents respectively optionally substituted phenylene or naphthylene,represents mono- or dicyclic heteroarylene having in each case 5 or 6 ring members or represents benzo-fused heteroarylene having 5 or 6 ring members, at least one of which in each case is oxygen, sulphur or nitrogen and one or two more of which optionally are nitrogen, wherein the substituents are selected from the group consisting of halogen, cyano, nitro, amino, hydroxyl, formyl, carboxyl, carbamoyl, thiocarbamoyl, represents straight-chain or branched alkyl, alkoxy, alkylthio, alkylsulphinyl or alkylsulphonyl having in each case 1 to 6 carbon atoms, represents straight-chain or branched alkenyl, alkenyloxy or alkinyloxy having in each case 2 to 6 carbon atoms, represents straight-chain or branched halogenoalkyl, halogenoalkoxy, halogenoalkylthio, halogenoalkylsulphinyl or halogenoalkyl sulphonyl having in each case 1 to 6 carbon atoms and 1 to 13 identical or different halogen atoms, represents straight-chain or branched halogenoalkenyl or halogenoalkenyloxy having in each case 2 to 6 carbon atoms and 1 to 13 identical or different halogen atoms, represents straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, alkylene or dioxyalkylene, each of which has 1 to 6 carbon atoms, is attached twice and is optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms, Ar² represents phenylene or naphthylene or represents heteroarylene having 3 to 7 ring members, each of the radicals being optionally mono- or polysubstituted by identical or different substituents and at least one of the 3 to 7 ring members being oxygen, sulphur or nitrogen and one or two more optionally being nitrogen, wherein the substitutents are selected from the group consisting of halogen, cyano, nitro, amino, hydroxyl, formyl, carboxyl, carbamoyl,thiocarbamoyl;

represents straight-chain or branched alkyl, alkoxy, alkylthio, alkylsulphinyl or alkylsulphonyl having in each case 1 to 6 carbon atoms;

represents straight-chain or branched alkenyl or alkenyloxy having in each case 2 to 6 carbon atoms;

represents straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;

alkylene or dioxyalkylene, each of which has 1 to 6 carbon atoms, is attached twice and is optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

E represents one of the groupings below:

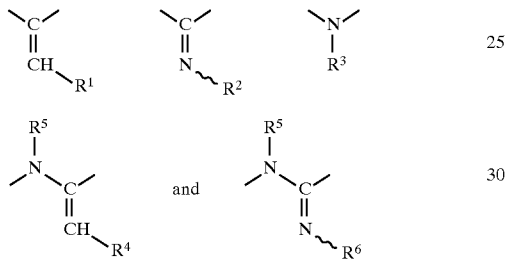

in which $R^1$ represents hydrogen, halogen, cyano or represents optionally halogen-, cyano- or $C_1$–$C_4$-alkoxy-substituted alkyl, alkoxy, alkylthio, alkylamino or dialkylamino having in each case 1 to 6 carbon atoms in the alkyl radicals, $R^2$ represents hydrogen, amino, cyano or represents optionally halogen-, cyano- or $C_1$–$C_4$-alkoxy-substituted alkyl, alkoxy, alkylamino or dialkylamino having in each case 1 to 6 carbon atoms in the alkyl radicals, $R^3$ represents hydrogen, cyano or represents optionally halogen-, cyano- or $C_1$–$C_4$-alkoxy-substituted alkyl, alkenyl or alkinyl having in each case up to 6 carbon atoms or represents optionally halogen-, cyano-, carboxyl-, $C_1$–$C_4$-alkyl- or $C_1$–$C_4$-alkoxy-carbonyl-substituted cycloalkyl or cycloalkylalkyl having 3 to 6 carbon atoms in the cycloalkyl moieties and optionally 1 to 4 carbon atoms in the alkyl moiety, $R^4$ represents hydrogen, halogen, cyano or represents optionally halogen-, cyano- or $C_1$–$C_4$-alkoxy-substituted alkyl, alkoxy, alkylthio, alkylamino or dialkylamino having in each case 1 to 6 carbon atoms in the alkyl radicals, $R^5$ represents alkyl having 1 to 6 carbon atoms and $R^6$ represents hydrogen, amino, cyano or represents optionally halogen-, cyano- or $C_1$–$C_4$-alkoxy-substituted alkyl, alkoxy, alkylamino or dialkylamino having in each case 1 to 6 carbon atoms in the alkyl radicals;

G represents a single bond, represents oxygen, sulphur or represents respectively optionally halogen-, hydroxyl-, $C_1$–$C_4$-alkyl-, $C_1$–$C_4$-halogenoalkyl- or $C_3$–$C_6$-cycloalkyl-substituted alkanediyl, alkenediyl, alkinediyl having in each case up to 4 carbon atoms or represents a substiuent selected from the group consisting of —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)n—CH$_2$—, —C(R$^7$)=N—O—, —C(R7)=N—O—CH$_2$—, —N(R$^8$)—, —CQ—N(R$^8$)—, —N(R$^8$)—CQ—, —Q—CQ—N(R$^8$)—, —N=C(R$^7$)—Q—CH$_2$—, —CH$_2$—O—N=C(R$^7$)—, —N(R$^8$)—CQ—Q—, —CQ—N(R$^8$)—CQ—Q—, —N(R$^8$)—CQ—Q—CH$_2$—, —Q—C(R$^7$)=N—O—CH$_2$—, —N(R$^8$)—C(R$^7$)=N—O—CH$_2$—, —O—CH$_2$—C(R$^7$)=N—O—, —N=N—C(R$^7$)=N—O—, —T—Ar$^3$ and —T—A$^3$—Q—, wherein n represents the numbers 0, 1 or 2, Q represents oxygen or sulphur, $R^7$ represents hydrogen, cyano, represents optionally halogen-, cyano- or $C_1$–$C_4$-alkoxy-substituted alkyl, alkoxy, alkylthio, alkylamino or dialkylamino having in each case 1 to 6 carbon atoms in the alkyl groups, or represents optionally halogen-, cyano-, carboxyl-, $C_1$–$C_4$-alkyl or $C_1$–$C_4$-alkoxy-carbonyl-substituted cycloalkyl having 3 to 6 carbon atoms, and $R^8$ represents hydrogen, hydroxyl, cyano or represents optionally halogen-, cyano- or $C_1$–$C_4$-alkoxy-substituted alkyl having 1 to 6 carbon atoms, or represents optionally halogen-, cyano-, carboxyl-, $C_1$–$C_4$-alkyl- or C1–C4-alkoxy-carbonyl-substituted cycloalkyl having 3 to 6 carbon atoms and Ar$^3$ represents phenylene, naphthylene, cycloalkylene or representsheteroarylene or heterocycloalkylene having 3 to 7 ring members, each of the radicals being optionally mono- or polysubstituted by identical or different substituents and at least one of the 3 to 7 ring members being oxygen, sulphur or nitrogen and one or two more optionally being nitrogen, wherein the substituents are selected from the group consisting of halogen, cyano, nitro, amino, hydroxyl, formyl, carboxyl, carbamoyl, and thiocarbamoyl represents straight-chain or branched alkyl, alkoxy, alkylthio,alkylsulphinyl or alkylsulphonyl having in each case 1 to 6 carbon atoms;

represents straight-chain or branched alkenyl or alkenyloxy having in each case 2 to 6 carbon atoms;

represents straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

represents straight-chain or branched halogenoalkenyl orhalogenoalkenyloxy having in each case 2 to 6 carbon atoms and 1 to 13 identical or different halogen atoms;

respectively straight-chain or branched alkylamino, dialkylamino,alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, and;

cycloalkyl having 3 to 6 carbon atoms and

T represents a single bond, represents oxygen, sulphur —CH$_2$—O—, CH$_2$—S— or represents alkanediyl having 1 to 3 carbon atoms, R represents alkyl, alkoxy, alkylamino, hydroxylamino, alkoxyamino ordialkylamino having in each case 1 to 4 carbon atoms.

3. Compounds of the formula (I) according to claim 1 in which

A represents methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-i-butylene, $Ar^1$ represents optionally substituted ortho-, meta- or paraphenylene, represents furanediyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl (in particular pyridine-2,3-diyl), pyrimidinediyl, pyridazinediyl, pyrazinediyl, 1,3,4-triazinediyl or 1,2,3-triazinediyl, wherein the substituents areselected from the group consisting of fluorine, chlorine, cyano, methyl, ethyl, cyclopropyl, trifluoromethyl, methoxy, ethoxy, methylthio, methylsulphinyl and methylsulphonyl, $Ar^2$ represents phenylene, naphthylene, furanediyl, thiophenediyl, oxazolediyl, isoxazolediyl, thiazolediyl, isothiazolediyl, 1,2,4-oxadiazolediyl, 1,3,4-oxadiazolediyl, 1,2,4-thiadiazolediyl, 1,3,4-thiadiazolediyl, pyridinediyl, pyrimidinediyl, pyridazinediyl, pyrazinediyl, I ,2,3-triazinediyl, 1,2,4-triazinediyl, 1,3,5-triazinediyl, each of which is optionally mono- to trisubstituted by identical or different substituents, wherein the substituents are selected from the groupconsisting of fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methy Isulphony loxy, ethylsulphonyloxy, hydroximinomethyl, hydroximinoethyl, methoximinomethyl, ethoximinomethyl, methoximinoethyl and ethoximinoethyl;

E represents a substituent selected from the group consisting of

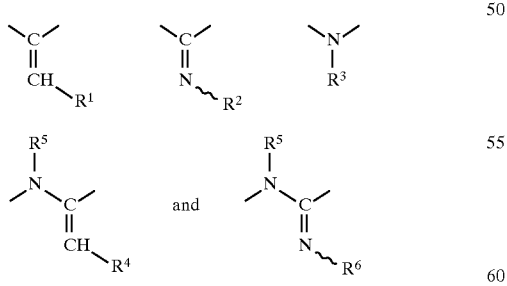

in which
hu 1represents hydrogen, fluorine, chlorine, bromine, cyano or represents optionally fluorine-, chlorine-, cyano-, methoxy- or ethoxy-substituted methyl, ethyl, propyl, methoxy, ethoxy, methylthio, ethylthio,methylamino, ethylamino or dimethylamino, $R^2$ represents hydrogen, amino, cyano or represents optionallyfluorine-, chlorine-, cyano-, methoxy- or ethoxy-substituted methyl, ethyl, methoxy, ethoxy, methylamino, ethylamino or dimethylamino, $R^3$ represents hydrogen, cyano or represents optionally fluorine-, cyano-, methoxy- or ethoxy-substituted methyl, ethyl, n- or i-propyl, n-, i- or s-butyl, represents allyl or propargyl or represents respectively optionally fluorine-, chlorine-, cyano-, carboxyl-, methyl-, ethyl-, n- or i-propyl-, methoxy-carbonyl- or ethoxy-carbonyl-substituted cyclopropyl, cyclobutyl, cyclopentyl, cyclohexyl, cyclopropylmethyl, cyclobutylmethyl, cyclopentylmethyl or cyclohexylmethyl, $R^4$ represents hydrogen, fluorine, chlorine, bromine, cyano or represents optionally fluorine-, chlorine-, cyano-, methoxy- or ethoxy-substituted methyl, ethyl, propyl, methoxy, ethoxy, methylthio, ethylthio, methylamino, ethylamino or dimethylamino, $R^5$ represents methyl, ethyl, n- or i-propyl, n-, i- or s-butyl, $R^6$ represents hydrogen, amino, cyano or represents optionally fluorine-, chlorine-, cyano-, methoxy- or ethoxy-substituted methyl, ethyl, methoxy, ethoxy, methylamino, ethylamino or dimethylamino, and G represents a single bond, represents oxygen, sulphur, or represents respectively optionally fluorine-, chlorine-, bromine-, hydroxyl-, methyl-, ethyl-, n- or i-propyl-, trifluoromethyl-, cyclopropyl-, cyclobutyl-, cyclopentyl- or cyclohexyl-substituted methylene, dimethylene (ethane-1,2-diyl), ethene-1,2-diyl, ethine-1,2-diyl or represents a substituent selected from the group consisting of

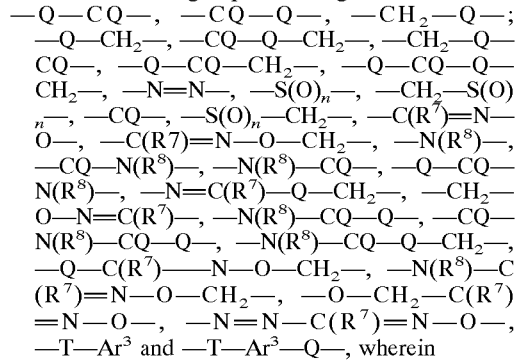

wherein n represents the numbers 0, 1 or 2,

Q represents oxygen or sulphur, $R^7$ represents hydrogen, cyano, represents optionally fluorine-, chlorine-, cyano-, methoxy- or etlioxy-substituted methyl, ethyl, n- or i-propyl, n-, i- or s-butyl, methoxy, ethoxy, propoxy, butoxy, methylthio, ethylthio, propylthio, butylthio, methylamino, ethylamino, propylamino, dimethylamino or diethylamino or represents optionally fluorine-, chlorine-, cyano-, carboxyl-, methyl-, ethyl-, n- or i-propyl-, methoxycarbonyl- or ethoxy-carbonyl-substituted cyclopropyl, cyclobutyl, cyclopentyl or cyclohexyl, and $R^8$ represents hydrogen, hydroxyl, cyano or represents optionally fluorine-, chlorine-, cyano-, methoxy- or ethoxy-substituted methyl, ethyl, n- or i-propyl, n-, i-, s- or t-butyl or. represents optionally fluorine-, chlorine-, cyano-, carboxyl-, methyl-, ethyl-, n- or i-propyl-, methoxy-carbonyl- or ethoxy-carbonyl-substituted cyclopropyl, cyclobutyl, cyclopentyl cyclohexyl, Ar³ represents phenylene, naphthylene, furanediyl, thiophenediyl, oxazolediyl, isoxazolediyl, thiazolediyl, isothiazolediyl, 1,2,4-oxadiazolediyl, 1,3,4-oxadiazolediyl, 1,2,4-thiadiazolediyl, 1,3,4-thiadiazolediyl, pyridinediyl, pyrimidinediyl, pyridazinediyl, pyrazinediyl, 1,2,3-triazinediyl, 1,2,4-triazinediyl, 1,3,5-triazinediyl, oxiranediyl, oxetanediyl, tetrahydrofuranediyl, perhydropyranediyl or pyrrolidinediyl, each of which is optionally mono- to trisubstituted, wherein the substituents are selected from the groud consisting of fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, , acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl, ethoximinoethyl and cyclopropyl and T represents a single bond, represents oxygen, sulphur, —CH₂—O—, CH₂—S—, methylene, ethylene or propylene and R represents methyl, ethyl, n- or i-propyl, methoxy, ethoxy, n- or i-propoxy, methylamino, ethylamino, n- or i-propylamino, hydroxylamino, methoxyamino, dimethylamino, diethylamino.

4. Compounds of the formula (1) according to claim 1 in which

A represents methylene, 1,1-ethylene, 1,2-ethylene, 1,2- or 1,3-propylene,

Ar¹ represents ortho-phenylene, pyridine-2,3-diyl or thiophene-2,3-diyl,

Ar² represents phenylene which is optionally mono- to trisubstituted by identical or different substituents, wherein the substituents are selected from the group consisting of fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluomethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, methylenedioxy and ethylenedioxy, each of which is attached twice and each of which is optionally mono- to tetrasubstituted by identical or different substituents selected from the group consisting of fluorine, chlorine, methyl, trifluoromethyl and ethyl, E represents a substituent selected from the group consisting of

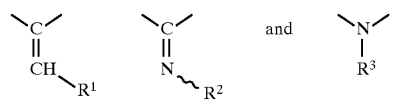

in which
R¹ and R² each represent methoxy and
R³ represents hydrogen, cyano, methyl, ethyl, n- or i-propyl, methoxy or ethoxy,
G represents oxygen or represents optionally fluorine-, chlorine- or bromine-substituted dimethylene (ethane-1,2-diyl), ethene-1,2-diyl or represents a substituent selected from the group consisting of —Q—CQ—, —CQ—Q—, —CH₂—Q—; —Q—CH₂—, —CQ—Q—CH₂—, —CH₂—Q—CQ—, —Q—CQ—CH₂—, —Q—CQ—Q—CH₂—, —N=N—, —S(O)ₙ—, —CH₂—S(O)ₙ—, —CQ—, —S(O)ₙ—CH₂—, —C(R⁷)=N—O—, —C(R7)=N—O—CH₂—, —N(R⁸)—, —CQ—N(R⁸)—, —N(R⁸)—CQ—, —Q—CQ—N(R⁸)—, —N=C(R⁷)—Q—CH₂—, —CH₂—O—N=C(R⁷)—, —N(R⁸)—CQ—Q—, —CQ—N(R⁸)—CQ—Q—, —N(R⁸)—CQ—Q—CH₂—, —Q—C(R⁷)=N—O—CH₂—, —N(R⁸)—C(R⁷)=N—O—CH₂—, —O—CH₂—C(R⁷)=N—O—, —N=N—C(R⁷)=N—O—, —T—Ar³ and —T—Ar³—Q—, wherein
n represents the numbers 0, 1 or 2,
Q represents oxygen or sulphur,
R⁷ represents hydrogen, cyano, methyl, ethyl or cyclopropyl and
R⁸ represents hydrogen, methyl, ethyl or cyclopropyl,
Ar³ represents phenylene, 1,2,4-thiadiazolediyl, 1,3,4-thiadiazolediyl, 1,2,4-oxadiazolediyl, 1,3,4-oxadiazolediyl, pyridinediyl, pyrimidinediyl, pyridazinediyl pyrazinediyl, 1,2,3-triazinediyl, 1,2,4-triazinediyl or 1,3,5-triazinediyl, each of which is optionally mono- to trisubstituted by identical or different substituents, wherein the substituents are selected from the group consisting of
fluorine, chlorine, bromine, cyano, methyl, ethyl, n- or i-propyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl and trifluoromethylsulphonyl, and T represents a single bond, represents oxygen, sulphur, —CH₂—O—, CH₂—S—, methylene, ethylene or propylene and R represents methyl, ethyl, methoxy, methylamino or hydroxylamino.

5. Compounds of the formula (I) according to claim 1 in which

A represents methylene, 1,1-ethylene, 1,2-ethylene, 1,2- or 1,3-propylene,

Ar¹ represents ortho-phenylene, pyridine-2,3-diyl or thiophene-2,3-diyl,

Ar² represents phenylene which is in each case optionally mono- to trisubstituted by identical or different substituents, wherein the substituents are selected from the group consisting of fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluomethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, methylenedioxy and ethylenedioxy, each of which is attached twice and each of which is optionally mono- to tetrasubstituted by identical or different substituents selected from the group consisting of fluorine, chlorine, methyl, trifluoromethyl or ethyl, E represents

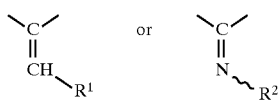

in which
R$^1$ and R$^2$ each represent methoxy and
G represents —O—CH$_2$ and
R represents methyl, ethyl, methoxy, methylamino or hydroxylamino.

6. Compounds of the formula (1) according to claim 1 in which

A represents methylene, 1,1-ethylene, 1,2-ethylene, 1,2- or 1,3-propylene,

Ar$^1$ represents ortho-phenylene, pyridine-2,3-diyl or thiophene-2,3-diyl,

Ar$^2$ represents phenylene which is optionally mono- to trisubstituted by identical or different substituent selected from the group consisting of
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluomethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximino ethyl, ethoximinoethyl, methylenedioxy and ethylenedioxy, each of which is attached twice and each of which is optionally mono- to tetrasubstituted by identical or different substituents selected from the group consisting of fluorine, chlorine, methyl, trifluoromethyl and ethyl, E represents

in which
R$^1$ and R$^2$ each represent methoxy and
G represents —C(R7)=N—O—CH$_2$— wherein R$^7$ represents hydrogen, cyano, methyl, ethyl or cyclopropyl and
R represents methyl, ethyl, methoxy, methyla mino or hydroxylamino.

7. Compounds of the formula (1) according to claim 1 in which

A represents methylene, 1,1-ethylene, 1,2-ethylene, 1,2- or 1,3-propylene,

Ar$^1$ represents ortho-phenylene,

Ar$^2$ represents phenylene which is optionally mono- to trisubstituted by identical or different substituents, wherein the substituents are selected from the group consisting of
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluomethoxy, difluorochloromethoxy, trifluoroethoxy, difluomethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, methylenedioxy and ethylenedioxy, each of which is attached twice and each of which is optionally mono- to tetrasubstituted by identical or different substituents selected from the group consisting of fluorine, chlorine, methyl, trifluoromethyl and ethyl, E represents

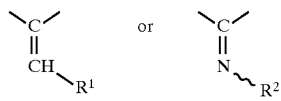

in which
R$^1$ and R$^2$ each represent methoxy,
G represents —T—Ar$^3$—Q— wherein
Q represents oxygen or sulphur,
Ar$^3$ represents 1,2,4-thiadiazolediyl, 1,3,4-thiadiazolediyl, 1,2,4-oxadiazolediyl, 1,3,4-oxadiazolediyl or represents pyridinediyl, pyrimidinediyl or 1,3,5-triazinediyl, each of which is optionally mono- or disubstituted by identical or different substituents selected from the group consisting of fluorine, chlorine cyano, methyl, cyclopropyl, methoxy, methylthio, trifluoromethyl, difluoromethoxy, trifluoromethoxy, and difluorochlioromethoxy, T represents a single bond, represents oxygen, sulphur, —CH$_2$—O—, CH$_2$—S—, methylene, ethylene or propylene and R represents methyl, ethyl, methoxy, methylamino or hydroxylamino.

8. An insecticidal composition comprising an insecticidally effective amount of according to claim 1 and an extender.

9. A method of combatting insects which comprises administering to such a locus from which it is desired to exclude such insects an insecticidally unt of a compound according to claim 1.

10. Process for preparing compounds of the formula (I) according to claim 1, comprising reacting a) hydroxyl compounds of the formula (II)

in which
    A and $Ar^2$ are each as defined in claim 1, with halogen compounds of the formula (III)

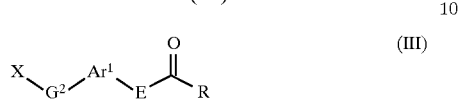

in which
    $G^2$ represents —Ar—Q— or represents —Ar—,
    $Ar^1$, $Ar^3$, E, Q and R are each as defined in claim 1 and
    X represents halogen, optionally in the presence of an acid acceptor and optionally in the presence of a diluent;
b) reacting hydroxyl compounds of the formula (II)

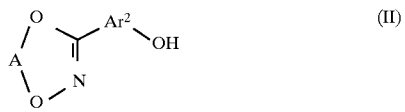

in which
    A and $Ar^2$ are each as defined in claim 1, with halogen compounds of formula (IV)

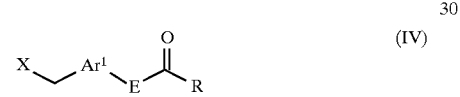

in which
    $Ar^1$, E and R are each as defined in claim 1 and
    X represents halogen, optionally in the presence of an acid acceptor and optionally in the presence of a diluent;
c) reacting esters of the formula (I-1)

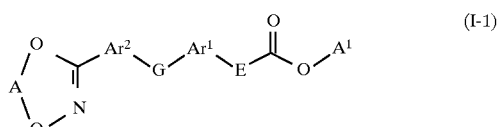

in which

A, $Ar^1$, $Ar^2$, E and G are each as defined in claim 1 and
    $A^1$ represents alkyl, with amines of the formula (V),

in which $A^2$ and $A^3$ independently of one another are each hydrogen, respectively optionally substituted alkyl, alkoxy or hydroxyl,
    or an acid addition complex thereof optionally in the presence of an acid acceptor and optionally in the presence of a diluent.

* * * * *